(12) United States Patent
Wennerholm et al.

(10) Patent No.: US 6,397,844 B1
(45) Date of Patent: Jun. 4, 2002

(54) RESPIRATION APPARATUS

(75) Inventors: Björn Wennerholm, Göteborg; Rolf Svensson, Jörlanda, both of (SE)

(73) Assignee: Barnwell Investments S.A. (PA)

( * ) Notice: Subject to any disclaimer, the term of this patent is extended or adjusted under 35 U.S.C. 154(b) by 0 days.

(21) Appl. No.: 09/693,944

(22) Filed: Oct. 23, 2000

Related U.S. Application Data

(63) Continuation of application No. PCT/SE99/00640, filed on Apr. 21, 1999.

(30) Foreign Application Priority Data

Apr. 23, 1998 (SE) ................................................ 9801421

(51) Int. Cl.$^7$ ............................ A61M 16/00; A62B 7/00
(52) U.S. Cl. ............................ 128/204.18; 128/204.24; 128/205.13; 128/205.17; 128/205.18; 417/413.1; 417/362; 417/521; 92/137; 92/98 R
(58) Field of Search ..................... 128/204.18, 204.24, 128/205.13, 205.17, 205.18; 417/413.1, 362, 521; 92/137, 98 R

(56) References Cited

U.S. PATENT DOCUMENTS

| | | | | |
|---|---|---|---|---|
| 3,225,758 A | * | 12/1965 | Morch | 128/204.24 |
| 3,379,194 A | * | 4/1968 | Ziermann | 128/204.24 |
| 3,646,933 A | * | 3/1972 | Monnier | 128/205.18 |
| 3,777,626 A | * | 12/1973 | Schurenberg et al. | 417/343 |
| 4,067,328 A | * | 1/1978 | Manley | 128/205.18 |
| 4,147,477 A | * | 4/1979 | Chardonneau et al. | 417/343 |
| 4,257,415 A | * | 3/1981 | Rubin | 128/200.21 |
| 4,409,977 A | * | 10/1983 | Bisera et al. | 128/205.15 |
| 4,495,947 A | | 1/1985 | Motycka | |
| 4,859,152 A | | 8/1989 | Kimura et al. | |
| 5,398,676 A | * | 3/1995 | Press et al. | 128/204.23 |
| 5,704,346 A | * | 1/1998 | Inoue | 128/204.24 |
| 6,237,589 B1 | * | 5/2001 | Denyer et al. | 128/200.21 |

FOREIGN PATENT DOCUMENTS

| | | |
|---|---|---|
| DE | 1917145 | 9/1970 |
| DE | 1917245 | 10/1970 |
| FR | 1525881 | 5/1968 |

* cited by examiner

*Primary Examiner*—John G. Weiss
*Assistant Examiner*—Michael Mendoza
(74) *Attorney, Agent, or Firm*—Birch, Stewart, Kolasch & Birch, LLP

(57) ABSTRACT

A portable apparatus for ventilation support to persons with respiratory distress is provided with a compressed air pump. The pump may be connected to the mouth or the nose via a tube for generation of pressure pulses with an individually adaptable air volume. The pump comprises a rigid container having two symmetrical halves and with a flexible membrane which is located as a laterally reciprocating diaphragm between the two container halves. These are provided with check valves permitting ambient air to be fed into the pump and from the pump into the tube while the membrane wall is moved, for generation of a pressure pulse. The pump is provided with a flexible pull device for reciprocating operation of the membrane in the container. The pull device extends via pulley wheels to a driving device located substantially in the same plane as the container and beside it.

19 Claims, 1 Drawing Sheet

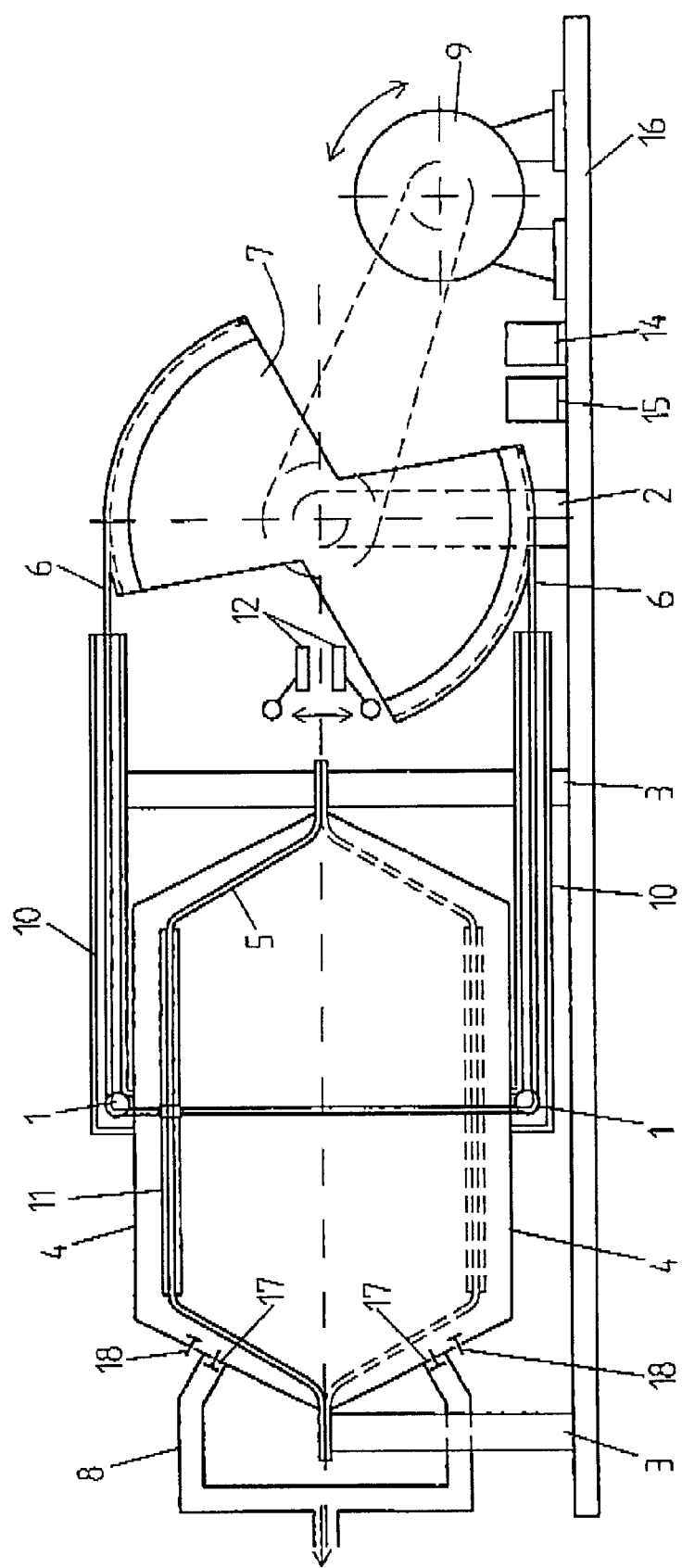

RESPIRATION APPARATUS

This application is a Continuation of PCT International Application No. PCT/SE99/00640 filed on Apr. 21, 1999, which designated the United States and on which priority is claimed under 35 U.S.C. § 120, the entire contents of which are hereby incorporated by reference.

TECHNICAL FIELD

The present invention relates to a portable apparatus for ventilation support to persons with respiratory distress, with a compressed air pump which may be connected to the mouth of the nose via tube means for generation of pressure pulses with an individually adaptable air volume, which pump comprises a rigid container consisting of two symmetrical halves and with a flexible membrane which is located as a laterally reciprocating diaphragm between the two container halves, that are provided with check valves permitting ambient air to be fed into the pump and from the pump into the tube means while the membrane wall is moved, for generation of a pressure pulse.

STATE OF THE ART

Prior art in the field of breathing aids, comprises portable units and non-portable units that, if required, may be moved inside a hospital or be used within an ambulance, but may not be comfortably carried when travelling, thereby fulfilling the criteria of being classed as portable. For example, apparatuses are available that provide oscillatory pulse types, IPPV, which apparatuses are heavy and expensive.

Conventional breathing aids for the above described area of use, often comprise a fan which creates a static overpressure, which is aimed to open and to ventilate the respiratory system of the user. However, this method, CPAP (Continuous Positive Air Pressure) lead to other drawbacks as noise, desiccation of the respiratory system and a high consumption of energy. Also, this method only works if the brain controls the diaphragm.

It is also known to use a piston or accordion pump for providing pressure pulses. However, these pump units are more bulky than fans and are normally combined with comparatively complicated electronics for synchronisation of the pump function to the user breathing rhythm. Accordingly, also these apparatuses have become energy demanding as well as expensive and unwieldy.

So far, membrane pumps have particularly been used on stationary apparatuses for spray painting, because they are normally very space consuming in comparison with fans and piston or accordion pumps.

Normally, the air requirement during sleep for the age of 18–80 years is about 7 liters per minute, for example the equivalent to 1 respiration of 0.6 liter every fifth second, while small children may respire about 30 times per minute with a corresponding smaller tidal volume. Accordingly, a breathing apparatus must have a relative wide capacity for adjustment, in order to cover occurring needs. This is difficult to achieve for single-action pumps.

OBJECT OF THE INVENTION

Therefore the object of the present invention is to provide a space-saving and simple apparatus which solves or at least reduces the above described problems.

THE SOLUTION

For this object, the invention is characterized in that the pump is provided with flexible pull means for reciprocating operation of the membrane in the container, said pull means extending via pulley wheels to a driving device located substantially in the same plane as the container and beside it. Because of this configuration of the invention, it is possible to use an efficient operating and power saving double action membrane pump.

Advantageous embodiments of the invention are disclosed by the accompanying claims.

BRIEF DESCRIPTION OF THE DRAWINGS

The invention will be further described in the following with reference to the accompanying drawing which schematically shows a section through a respiration apparatus according to the invention.

DETAILED DESCRIPTION OF THE INVENTION

The respiration apparatus according to the invention provides for a comprehensive ventilation support wherever the patient is, showing to that it is designed for fulfilling the following demands:

a) low weight
b) small dimensions, to be able to fit inside cabin luggage
c) low power consumption
d) be equipped with internal, chargable storage battery,
e) possibility to operate from 220 V 50 Hz AC-mains
f) alternatively 12/24 V direct-current battery
g) simple to adjust and use
h) dependable in service
i) low sound level
j) low manufacturing cost The apparatus comprises a pump with a rigid container consisting of two symmetrical container halves 4 manufactured from plastic or aluminium. A membrane 5 of a flexible material is mounted between the two container halves and is provided with a central stiffener 11. The thus formed pump housing is rigidly attached to the base plate 16 which also carries a drive motor 9 and pendulum barrel 7 via a bearing bracket 2.

Pull means 6 are mounted at the respective side of the stiffener 11, in such a manner that each pull means extends through an opening in the respective container half 4, to which opening a guide-rail 10 connects sealingly. The pull means may for example comprise smooth or toothed belts extending via pulley wheels 1 to openings at the outer ends of the guide-rails. These openings have substantially the same shape as the cross section of the smooth or toothed belt forming sealing segments having a certain length, for providing sealing against the smooth or toothed belt along a corresponding longitudinal section.

The drive motor 9 turns the pendulum barrel 7 in a reciprocating motion, and the length of these movements is defined by adjustably arranged limit switches 12 that reverses the current supply of the drive motor via a relay 14. The frequency of the movement is defined by an adjustable time relay 15. Each container half 4 is provided with check valve controlled air inlets 18 and outlets 17 respectively, where the outlets 17 are interconnected at 8 to a mutual inspiration tube 8 (expiration from pump—inspiration to patient).

The above described, compact built ventilator is preferably positioned below the bed and is connected to the electricity supply network via a 12 V DC battery eliminator, alternatively 12 V socket when staying in a caravan/mobile home etc. A standard patient mask with expiration valve is preferably positioned over the mouth and is connected to the air outlet 8. After a switch is closed, a pre-set air volume is provided with a frequency which can be adapted to the age and weight of the patient. The amplitude of the membrane depends upon the pre-set rotation angle of the pendulum barrel. A double action is achieved due to that a corresponding air volume which is delivered when the membrane moves in one direction, is at the same time drawn in at the opposite side of the membrane. As a consequence, separate intake phase is eliminated with an accompanying saving of energy, wear and time. The last point is important for high frequencies.

As an alternative to the above described adjustable operation of the pendulum barrel 7, this may be connected to the drive motor 9 via a simple crankshaft for conversion of a rotating motion into a reciprocating motion. For this, no limit switches and no relay for polarity reversal of the drive motor power supply will be needed. In this case, the transmission, i.e. the speed and transmission ratio of the drive motor determines the working frequency of the respiration apparatus. It has been found that the respiration rate of the human body can easily adapt to such a suitable working frequency.

The invention is not limited to the above described embodiment, but several variants are imaginable within the scope of the following claims.

What is claimed is:

1. A portable apparatus for ventilation support to persons with respiratory distress comprises:

a tube device for connection to a mouth or nose;

a compressed air pump for generating of pressure pulses with an individually adaptable air volume, the pump being connected to the tube device and including a rigid container having two halves with a flexible membrane therebetween, the flexible membrane being laterally displaceable between the two container halves, each container half having check valves for permitting ambient air to be fed into the pump and from the pump to the tube device when the flexible membrane is moved to generate a pressure pulse;

flexible pull means for reciprocating the flexible membrane in the container, the pull means extending via pulley wheels into the air pump; and a driving device located adjacent to the container, the driving device being connected to the pull means for moving the pull means to reciprocate the flexible membrane.

2. The portable apparatus according to claim 1, wherein the two halves of the air pump are symmetrical.

3. The portable apparatus according to claim 1, wherein a shape of the membrane corresponds to a shape of the container halves.

4. The portable apparatus according to claim 1, wherein the driving device is located substantially in a same plane as the rigid container.

5. The portable apparatus according to claim 4, wherein the flexible membrane is connected to the rigid container at a location which coincides with the plane in which the driving device is located.

6. The portable apparatus according to claim 1, wherein the pull means extends through an opening at a center of each of the container halves and wherein a guide rail is located adjacent each of the openings, the guide rail forming a seal between an interior of the rigid container and surrounding atmosphere.

7. The portable apparatus according to claim 6, wherein the pull means comprises a toothed belt and wherein the guide rail is provided with an aperture segment for the toothed belt, the segment substantially corresponds to a cross section of the toothed belt for sealing against the belt.

8. The portable apparatus according to claim 7, wherein a sealing segment has a length in order to provide a sealing against the toothed belt along a corresponding longitudinal section of the belt.

9. The portable apparatus according to claim 6, wherein the pull means comprises a belt, the guide rail being provided with an aperture segment for the belt, the segment substantially corresponds to a cross section of the belt for sealing against the belt.

10. The portable apparatus according to claim 9, wherein a sealing segment has a length in order to provide a sealing against the belt along a corresponding longitudinal section of the belt.

11. The portable apparatus according to claim 1, further comprising a pendulum barrel which is rotatable around an axis and wherein the pull means is attached to a center of the membrane and respective ends of the pull means are mounted to the pendulum barrel.

12. The portable apparatus according to claim 11, wherein the flexible membrane is in a plane which is substantially parallel to the axis in which the pendulum barrel rotates.

13. The portable apparatus according to claim 11, wherein the pendulum barrel is attached to the driving device via a crankshaft for conversion of a rotating movement to a reciprocating movement.

14. The portable apparatus according to claim 11, wherein the driving device is connected to the pendulum barrel via a toothed belt transmission.

15. The portable apparatus according to claim 14, wherein the pendulum barrel is operated by polarity reversal of a DC motor, via limit switches and time relay in order to provide rapid membrane movements and pump action by absence of a separate intake stroke.

16. The portable apparatus according to claim 15, wherein the limit switches are readily repositionable in order to determine a volume of each separate intake stroke.

17. The portable apparatus according to claim 11, wherein the driving device is connected to the pendulum barrel via a belt transmission.

18. The portable apparatus according to claim 17, wherein the pendulum barrel is operated by polarity reversal of a DC motor, via limit switches and time relay in order to provide rapid membrane movements and pump action by absence of a separate intake stroke.

19. The portable apparatus according to claim 18, wherein the limit switches are readily repositionable in order to determine a volume of each separate intake stroke.

* * * * *